US009204813B2

(12) United States Patent
Kaib et al.

(10) Patent No.: US 9,204,813 B2
(45) Date of Patent: Dec. 8, 2015

(54) METHOD OF DETECTING SIGNAL CLIPPING IN A WEARABLE AMBULATORY MEDICAL DEVICE

(71) Applicant: ZOLL MEDICAL CORPORATION, Chelmsford, MA (US)

(72) Inventors: Thomas E. Kaib, North Huntingdon, PA (US); Shane S. Volpe, Saltsburg, PA (US); John D. Macho, Farmington, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 14/451,046

(22) Filed: Aug. 4, 2014

(65) Prior Publication Data

US 2015/0080699 A1   Mar. 19, 2015

Related U.S. Application Data

(60) Continuation of application No. 14/064,403, filed on Oct. 28, 2013, now Pat. No. 8,798,729, which is a division of application No. 13/428,891, filed on Mar. 23, 2012, now Pat. No. 8,600,486.

(60) Provisional application No. 61/467,532, filed on Mar. 25, 2011.

(51) Int. Cl.
*A61B 5/04* (2006.01)
*A61B 5/0408* (2006.01)
(Continued)

(52) U.S. Cl.
CPC ........... *A61B 5/04014* (2013.01); *A61B 5/0408* (2013.01); *A61B 5/04085* (2013.01);
(Continued)

(58) Field of Classification Search
None
See application file for complete search history.

(56) References Cited

U.S. PATENT DOCUMENTS 2,688,752 A   9/1954 Sbarra et al.
3,241,556 A   3/1966 Zacouto
(Continued)

FOREIGN PATENT DOCUMENTS

EP   396048 A1   11/1990
EP   0295497 B1   9/1993
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.

(Continued)

*Primary Examiner* — Brian T Gedeon
*Assistant Examiner* — Ankit Tejani
(74) *Attorney, Agent, or Firm* — Lando & Anastasi, LLP

(57) ABSTRACT

A wearable medical device and method of detecting clipping of ECG signals is disclosed. In one embodiment, the wearable medical device comprises a plurality of ECG sensing electrodes configured to sense an ECG of a patient and an ECG acquisition circuit electrically coupled to a pair of the plurality of ECG sensing electrodes and configured to provide an amplified and conditioned analog ECG signal, a programmable attenuation/gain stage electrically coupled between a first gain stage and a second gain stage, an ADC electrically coupled to the ECG acquisition circuit to receive and digitize the amplified and conditioned analog ECG signal and provide a digitized ECG signal, and a signal conditioning and control unit electrically coupled to the ECG acquisition circuit and the ADC to receive and monitor the digitized ECG signal and to detect clipping of the amplified and conditioned analog ECG signal based upon the digitized ECG signal.

13 Claims, 3 Drawing Sheets

(51) Int. Cl.
 *A61B 5/0428* (2006.01)
 *A61B 5/00* (2006.01)
 *H03G 7/00* (2006.01)
(52) U.S. Cl.
 CPC ......... *A61B5/04286* (2013.01); *A61B 5/4836* (2013.01); *A61B 5/6805* (2013.01); *A61B 5/6831* (2013.01); *H03G 7/002* (2013.01); *H03G 7/005* (2013.01)

(56) References Cited

U.S. PATENT DOCUMENTS

| | | |
|---|---|---|
| 3,409,007 A | 11/1968 | Fuller |
| 3,460,542 A | 8/1969 | Gemmer |
| 3,553,651 A | 1/1971 | Bird et al. |
| 3,664,560 A | 5/1972 | Perkins |
| 3,702,613 A | 11/1972 | Panico et al. |
| 3,706,313 A | 12/1972 | Milani et al. |
| 3,724,455 A | 4/1973 | Unger |
| 3,744,482 A | 7/1973 | Kaufman et al. |
| 3,826,245 A | 7/1974 | Funfstuck |
| 3,862,636 A | 1/1975 | Bell et al. |
| 3,886,950 A | 6/1975 | Ukkestad et al. |
| 3,897,785 A | 8/1975 | Barto, Jr. |
| 3,942,533 A | 3/1976 | Cannon, III |
| 3,961,623 A | 6/1976 | Milani et al. |
| 4,002,239 A | 1/1977 | Buchalter |
| 4,088,138 A | 5/1978 | Diack et al. |
| 4,094,310 A | 6/1978 | McEachern et al. |
| 4,136,690 A | 1/1979 | Anderson et al. |
| 4,576,170 A | 3/1986 | Bradley et al. |
| 4,580,572 A | 4/1986 | Granek et al. |
| 4,583,547 A | 4/1986 | Granek et al. |
| 4,608,987 A | 9/1986 | Mills |
| 4,619,265 A | 10/1986 | Morgan et al. |
| 4,632,122 A | 12/1986 | Johansson et al. |
| 4,679,572 A | 7/1987 | Baker, Jr. |
| 4,698,848 A | 10/1987 | Buckley |
| 4,729,377 A | 3/1988 | Granek et al. |
| 4,823,796 A | 4/1989 | Benson |
| 4,889,131 A | 12/1989 | Salem et al. |
| 4,926,879 A | 5/1990 | Sevrain et al. |
| 4,928,690 A | 5/1990 | Heilman et al. |
| 4,938,231 A | 7/1990 | Milijasevic et al. |
| 4,978,926 A | 12/1990 | Zerod et al. |
| 4,991,217 A | 2/1991 | Garrett et al. |
| 5,000,189 A | 3/1991 | Throne et al. |
| 5,007,427 A | 4/1991 | Suzuki et al. |
| 5,062,834 A | 11/1991 | Gross et al. |
| 5,078,134 A | 1/1992 | Heilman et al. |
| 5,097,830 A | 3/1992 | Eikefjord et al. |
| 5,224,479 A | 7/1993 | Sekine |
| 5,225,763 A | 7/1993 | Krohn et al. |
| 5,306,956 A | 4/1994 | Ikeda et al. |
| 5,342,404 A | 8/1994 | Alt et al. |
| 5,348,008 A | 9/1994 | Bornn et al. |
| 5,357,696 A | 10/1994 | Gray et al. |
| 5,361,412 A | 11/1994 | Perry |
| 5,365,932 A | 11/1994 | Greenhut |
| 5,371,692 A | 12/1994 | Draeger et al. |
| 5,381,798 A | 1/1995 | Burrows |
| 5,405,361 A | 4/1995 | Persson |
| 5,413,262 A | 5/1995 | Dewire et al. |
| 5,433,737 A | 7/1995 | Aimone |
| 5,443,494 A | 8/1995 | Paolizzi et al. |
| 5,470,341 A | 11/1995 | Kuehn et al. |
| 5,544,661 A | 8/1996 | Davis et al. |
| 5,558,640 A | 9/1996 | Pfeiler et al. |
| 5,601,612 A | 2/1997 | Gliner et al. |
| 5,606,242 A | 2/1997 | Hull et al. |
| 5,607,454 A | 3/1997 | Cameron et al. |
| 5,611,085 A | 3/1997 | Rasmussen |
| 5,619,117 A | 4/1997 | Koenck |
| 5,625,291 A | 4/1997 | Brink et al. |
| 5,662,689 A | 9/1997 | Elsberry et al. |
| 5,701,894 A | 12/1997 | Cherry et al. |
| 5,708,978 A | 1/1998 | Johnsrud |
| 5,718,242 A | 2/1998 | McClure et al. |
| 5,721,482 A | 2/1998 | Benvegar et al. |
| 5,724,025 A | 3/1998 | Tavori |
| 5,730,143 A | 3/1998 | Schwarzberg |
| 5,738,102 A | 4/1998 | Lemelson |
| 5,741,306 A | 4/1998 | Glegyak et al. |
| 5,758,366 A | 6/1998 | Wilson |
| 5,758,443 A | 6/1998 | Pedrazzini |
| 5,772,604 A | 6/1998 | Langberg et al. |
| 5,792,190 A | 8/1998 | Olson et al. |
| 5,824,017 A | 10/1998 | Sullivan et al. |
| 5,827,196 A | 10/1998 | Yeo et al. |
| 5,830,236 A | 11/1998 | Mouchawar et al. |
| 5,833,714 A | 11/1998 | Loeb |
| 5,887,978 A | 3/1999 | Lunghofer et al. |
| 5,924,979 A | 7/1999 | Swedlow et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,208,896 B1 | 3/2001 | Mulhauser |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,390,996 B1 | 5/2002 | Halperin et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,681,003 B2 | 1/2004 | Linder et al. |
| 6,687,523 B1 | 2/2004 | Jayaramen et al. |
| 6,690,969 B2 | 2/2004 | Bystrom et al. |
| 6,694,191 B2 | 2/2004 | Starkweather et al. |
| 6,804,554 B2 | 10/2004 | Ujhelyi et al. |
| 6,827,695 B2 | 12/2004 | Palazzolo et al. |
| 6,889,078 B2 | 5/2005 | Struble et al. |
| 6,889,079 B2 | 5/2005 | Bocek et al. |
| 6,908,437 B2 | 6/2005 | Bardy |
| 6,961,612 B2 | 11/2005 | Elghazzawi et al. |
| 6,990,373 B2 | 1/2006 | Jayne et al. |
| 7,130,690 B2 | 10/2006 | Rueter et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,600,486 B2 | 12/2013 | Kaib et al. |
| 2001/0031991 A1 | 10/2001 | Russial |
| 2002/0077689 A1 | 6/2002 | Kirkland |
| 2003/0004547 A1 | 1/2003 | Owen et al. |
| 2003/0032988 A1 | 2/2003 | Fincke |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0216786 A1 | 11/2003 | Russial |
| 2004/0007970 A1 | 1/2004 | Ma et al. |
| 2004/0049233 A1 | 3/2004 | Edwards |
| 2004/0143297 A1 | 7/2004 | Ramsey |
| 2004/0162510 A1 | 8/2004 | Jayne et al. |
| 2004/0249419 A1 | 12/2004 | Chapman et al. |

(56) References Cited

U.S. PATENT DOCUMENTS

| | | |
|---|---|---|
| 2005/0049515 A1 | 3/2005 | Misczynski et al. |
| 2005/0131465 A1 | 6/2005 | Freeman et al. |
| 2005/0144043 A1 | 6/2005 | Holland et al. |
| 2005/0246199 A1 | 11/2005 | Futch |
| 2005/0283198 A1 | 12/2005 | Haubrich et al. |
| 2006/0036292 A1 | 2/2006 | Smith et al. |
| 2006/0085049 A1 | 4/2006 | Cory et al. |
| 2006/0095091 A1 | 5/2006 | Drew |
| 2006/0178706 A1 | 8/2006 | Lisogurski et al. |
| 2006/0211934 A1 | 9/2006 | Hassonjee et al. |
| 2006/0220809 A1 | 10/2006 | Stigall et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0161913 A1 | 7/2007 | Farrell et al. |
| 2007/0162390 A1 | 7/2007 | Pancholy et al. |
| 2007/0169364 A1 | 7/2007 | Townsend et al. |
| 2007/0239214 A1 | 10/2007 | Cinbis |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0058884 A1 | 3/2008 | Matos |
| 2008/0097793 A1 | 4/2008 | Dicks et al. |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0183090 A1 | 7/2008 | Farringdon et al. |
| 2008/0249591 A1 | 10/2008 | Gaw et al. |
| 2008/0287749 A1 | 11/2008 | Reuter |
| 2008/0294019 A1 | 11/2008 | Tran |
| 2008/0312520 A1 | 12/2008 | Rowlandson et al. |
| 2008/0312522 A1 | 12/2008 | Rowlandson et al. |
| 2009/0018428 A1 | 1/2009 | Dias et al. |
| 2009/0066366 A1 | 3/2009 | Solomon |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0118808 A1 | 5/2009 | Belacazar et al. |
| 2009/0138059 A1 | 5/2009 | Ouwerkerk |
| 2009/0212984 A1 | 8/2009 | Baker |
| 2009/0231124 A1 | 9/2009 | Klabunde et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0307266 A1 | 12/2009 | Fleizach et al. |
| 2009/0318779 A1 | 12/2009 | Tran |
| 2010/0010559 A1 | 1/2010 | Zhang et al. |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0081962 A1 | 4/2010 | Hamaguchi et al. |
| 2010/0114243 A1 | 5/2010 | Nowak et al. |
| 2010/0171611 A1 | 7/2010 | Gao et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0015533 A1 | 1/2011 | Cox et al. |
| 2011/0022105 A9 | 1/2011 | Owen et al. |
| 2011/0093840 A1 | 4/2011 | Pynenburg et al. |
| 2011/0098765 A1 | 4/2011 | Patel |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0016361 A1 | 1/2012 | White et al. |
| 2012/0053479 A1 | 3/2012 | Hopenfeld |
| 2012/0112903 A1 | 5/2012 | Kaib et al. |
| 2012/0146797 A1 | 6/2012 | Oskin et al. |
| 2012/0158075 A1 | 6/2012 | Kaib et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2013/0085538 A1 | 4/2013 | Volpe et al. |
| 2013/0231711 A1 | 9/2013 | Kaib |

FOREIGN PATENT DOCUMENTS

| | | |
|---|---|---|
| EP | 0335356 B1 | 3/1996 |
| EP | 0707825 A2 | 4/1996 |
| EP | 0761255 A1 | 3/1997 |
| EP | 1455640 B1 | 1/2008 |
| EP | 1720446 B1 | 7/2010 |
| JP | 5115450 A | 5/1993 |
| JP | 2002200059 A | 7/2002 |
| WO | 9722297 A1 | 6/1997 |
| WO | 9839061 A2 | 9/1998 |
| WO | 9843537 A1 | 10/1998 |
| WO | 9959465 A1 | 11/1999 |
| WO | 0002484 A1 | 1/2000 |
| WO | 0030529 A1 | 6/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2006050325 A3 | 9/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |
| WO | 2010077997 A3 | 10/2010 |

OTHER PUBLICATIONS

DeBock, et al., "Captopril treatment of chronic heart failure in the very old," J. Gerontol. (1994) 49: M148-M152.

Notification of Transmittal of the International Search Report and the Written Opinion of the International Searching Authority, of the Declaration mailed Aug. 10, 2012, for International Application No. PCT/US2012/030356, 14 pages.

O'Keeffe et al., "Reproducability and responsiveness of quality of life assessment and six minute walk test in elderly heart failure patients," Heart (1998) 80: 377-382.

METHOD OF DETECTING SIGNAL CLIPPING IN A WEARABLE AMBULATORY MEDICAL DEVICE

RELATED APPLICATIONS

This application is a continuation of U.S. patent application Ser. No. 14/064,403, titled "METHOD OF DETECTING SIGNAL CLIPPING IN A WEARABLE AMBULATORY MEDICAL DEVICE," filed Oct. 28, 2013, which is a division of U.S. patent application Ser. No. 13/428,891, titled "METHOD OF DETECTING SIGNAL CLIPPING IN A WEARABLE AMBULATORY MEDICAL DEVICE," filed Mar. 23, 2012, which claims priority under 35 U.S.C. §119(e) to U.S. Provisional Application Ser. No. 61/467,532, titled "METHOD OF DETECTING SIGNAL CLIPPING IN A WEARABLE AMBULATORY MEDICAL DEVICE," filed on Mar. 25, 2011, each of which is hereby incorporated herein by reference in its entirety.

BACKGROUND

1. Field of the Invention

The present invention is generally directed to the processing of electrical signals, and more particularly to the processing of ECG signals and the treatment of cardiac conditions in an ambulatory medical device, such as a wearable defibrillator.

2. Discussion of the Related Art

To protect against cardiac arrest and other cardiac health ailments, some at-risk patients may use a wearable defibrillator, such as the LifeVest® wearable cardioverter defibrillator available from ZOLL Medical Corporation of Chelmsford, Mass. To remain protected, the patient wears the device nearly continuously while going about their normal daily activities.

With an ambulatory medical device, such as a wearable defibrillator, the patient's electrocardiogram (ECG) signal is obtained from body surface electrodes. When the ECG signal is obtained in this manner, electrical noise frequently degrades the quality of the ECG signal. The challenge becomes one of extracting a clean ECG signal from the sometimes noisy signals derived from the body-surface electrodes. A typical ECG measurement system includes a signal acquisition circuit (also called an analog front end (AFE)) that amplifies the ECG signals gathered by the electrodes, an analog-to-digital converter (ADC) that digitizes the amplified ECG signals and a processor that analyzes the ECG signals and controls the ambulatory medical device based on the processed ECG signals.

The ECG signals provided by the electrodes are typically about 80 microvolts to about 2 millivolts in signal amplitude. The typical signal acquisition circuit amplifies the ECG signals received from the body surface electrodes by about 500 to 1000 times before providing the amplified ECG signal to the ADC to digitize the ECG signal. Unfortunately, any to amplification of the ECG signal also amplifies any noise present in the ECG signal. To maximize the signal-to-noise ratio and reduce noise in the system, the amplification of the ECG signal is completed in multiple stages. These multiple stages typically include one or more amplifier or gain stages and a controlled or programmable attenuation stage. However, these multiple amplifier stages can make the system susceptible to analog and/or digital signal clipping. As defined herein, clipping is a form of signal distortion that cuts off or "clips" the signal once the gain of the amplifier exceeds a certain threshold or when the ADC is at its minimum or maximum voltage range. Typically, the threshold above which analog clipping occurs is the maximum output level of the amplifier.

Consequences of analog clipping can include distorted ECG signals presented to the ADC input. In addition, once analog clipping starts to occur, the ECG signal being processed by the signal acquisition circuit will no longer respond to the control signals sent by the system and can cause the signal acquisition system to malfunction.

SUMMARY

At least one aspect is directed to a wearable medical device. The wearable medical device comprises a plurality of ECG sensing electrodes configured to sense an ECG of a patient and an ECG acquisition circuit electrically coupled to a pair of the plurality of ECG sensing electrodes and configured to provide an amplified and conditioned analog ECG signal. The ECG acquisition circuit including a programmable attenuation/gain stage electrically coupled between a first gain stage and a second gain stage. The wearable medical device also includes an analog to digital converter electrically coupled to the ECG acquisition circuit to receive and digitize the amplified and conditioned analog ECG signal and provide a digitized ECG signal. The wearable medical device further includes a signal conditioning and control unit electrically coupled to the ECG acquisition circuit and the analog to digital converter to receive and monitor the digitized ECG signal and to detect clipping of the amplified and conditioned analog ECG signal based upon the digitized ECG signal.

In some embodiments, the signal conditioning and control unit includes an automatic level control unit electrically coupled to the programmable attenuation/gain stage, and configured to vary an amount of attenuation/gain provided by the programmable to attenuation/gain stage based on the digitized ECG signal.

In one embodiment, the automatic level control unit is configured to determine whether a voltage level of the digitized ECG signal is above a threshold level and configured to increase the amount of attenuation provided by the programmable attenuation/gain stage. The automatic level control unit can be configured to determine whether a voltage level of the digitized ECG signal is below a threshold level and configured to decrease the amount of attenuation provided by the programmable attenuation/gain stage.

In another embodiment, the signal conditioning and control unit includes an analog clipping detection and control unit electrically coupled to the programmable attenuation/gain stage, and configured to determine whether a voltage level is approaching a clipping threshold. The analog clipping detection and control unit can be configured to determine the voltage level before programmable attenuation/gain stage. The amplified and conditioned analog ECG signal can be marked as compromised in response to a determination that the voltage level is approaching the clipping threshold before the programmable attenuation/gain stage.

In some embodiments, the analog clipping detection and control unit is configured to determine the voltage level after the programmable attenuation/gain stage. The analog clipping detection and control unit can attenuate the amplified and conditioned analog ECG signal in response to a determination that the voltage level is approaching the clipping threshold after the programmable attenuation/gain stage. The clipping threshold can be determined based on a voltage range of an ECG of a human patient, a maximum output voltage level and a current gain setting of at least one of the first gain, the programmable attenuation/gain stage and the second gain stage.

The wearable medical device can include a low noise instrumentation amplifier electrically coupled to the pair of the plurality of ECG sensing electrodes and the first gain stage. The wearable medical device can also include a low pass filter electrically coupled to at least one of the second gain stage and the analog to digital converter.

At least one aspect is directed to a method of detecting clipping of ECG signals in a wearable medical device. The method comprises acts of sensing an ECG signal of a patient using ECG sensing electrodes and amplifying the sensed ECG signal using a first gain stage. The method also includes an act of conditioning the amplified ECG signal from the first gain stage using a programmable attenuation/gain stage and amplifying the conditioned ECG signal from the programmable attenuation/gain stage using a second gain stage. The method further includes an act of receiving and digitizing the amplified and conditioned analog ECG signal to provide a digitized ECG signal and monitoring the digitized ECG signal to detect clipping of the amplified and conditioned analog ECG signal based upon the digitized ECG signal.

The method further includes an act of varying an amount of attenuation applied by the programmable attenuation/gain stage based on the digitized ECG signal. The act of varying the amount may include an act of determining whether a voltage level of the digitized ECG signal is above a threshold level and increasing the amount of attenuation applied by the programmable attenuation/gain stage.

In one embodiment, the act of varying the amount includes the acts of determining whether a voltage level of the digitized ECG signal is below a threshold level and decreasing the amount of attenuation applied by the programmable attenuation/gain stage. In some embodiments, the act of varying the amount includes the acts of determining whether a voltage level is approaching a clipping threshold. In one embodiment, method further includes determining the clipping threshold based on a voltage range of an ECG of a human patient, a current gain setting and a maximum output voltage level of at least one of the first gain stage, the programmable attenuation/gain stage and the second gain stage.

In some embodiments, the act of determining includes the act of marking the amplified and conditioned analog ECG signal as compromised in response to a determination that the voltage level is approaching the clipping threshold before programmable attenuation/gain stage. The act of determining can include the act of attenuating the amplified and conditioned analog ECG signal in response to a determination that the voltage level is approaching the clipping threshold after the programmable attenuation/gain stage. Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not to necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
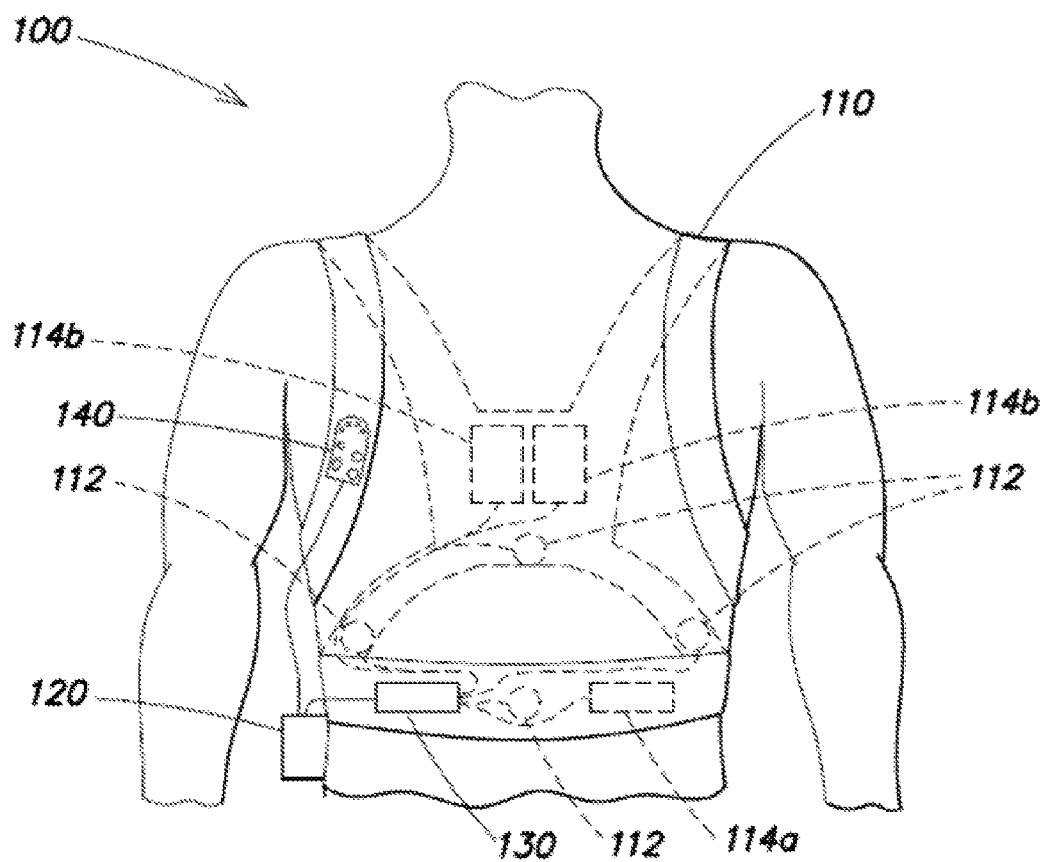
FIG. 1 illustrates a wearable medical device, such as a wearable defibrillator, in accordance with an embodiment of the present invention.

Applicant has appreciated that because any amount of clipping can distort the quality of the ECG signal, it would be desirable to detect such clipping, and where possible, to mitigate it. It would also be desirable to have the ECG signal detected by the analog signal acquisition circuit to be free of clipping distortions before that ECG signal passes to the analog-to-digital converter (ADC). Distortion of the ECG signal in the signal acquisition circuit can result in any processing that is based upon that distorted ECG signal being unreliable. For example, in a wearable defibrillator, the distortion of the ECG signal due to clipping may result in a false to positive detection of arrhythmia, or worse, the failure to detect an arrhythmia. A false positive detection of arrhythmia can result in the wearable defibrillator initiating a treatment sequence, which if not terminated by the patient, could deliver an unnecessary shock to the patient. The amplification of noise present in the ECG signal may also overdrive the signal acquisition circuitry, resulting in a near zero output, causing the system to falsely detect a state of no cardiac electrical activity (asystole). Conversely, a failure to detect an actual arrhythmia can result in a failure to initiate a treatment sequence and result in serious risk for the patient.

Accordingly, a system and method is described herein that can detect whether clipping of the ECG signal has occurred at any of the amplification or gain stages of a signal acquisition circuit. The system and method are able to either correct the ECG signal, to warn a control unit of the unreliability of the ECG signal, or both.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Moreover, it is to be understood that both the foregoing information and the following detailed description are merely illustrative examples of various aspects and embodiments of the present invention, and are intended to provide an overview or framework for understanding the nature and character of the claimed aspects and embodiments. Any embodiment disclosed herein may be combined with any other embodiment in any manner consistent with at least one of the aspects disclosed herein, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearance of such terms herein is not necessarily all referring to the same embodiment.

Embodiments of the present invention are directed to an electrode system that may be to used in a wearable medical device, such as that described in U.S. Pat. No. 5,944,669 (hereinafter "the '669 patent"), which is incorporated herein by reference in its entirety, to monitor cardiac function, to initiate treatment of a detected cardiac condition, or both. The '669 patent describes a method and apparatus for sensing cardiac function in a patient that may be used to initiate treatment of a detected cardiac condition. ECG sensing electrodes are used to obtain ECG signals from the heart of the patient and those ECG signals are analyzed using various techniques to provide information indicative of the operation of the patient's heart, and whether a treatable cardiac condition is present for which treatment should be initiated. In accordance with an aspect of the present invention, the signals received from the pairs of ECG sensing electrodes described in the '669 patent may be processed in a manner described in detail below so that the presence of ECG signal clipping is identified and/or corrected thereby improving reliability in detection of the ECG signals and any further processing of those ECG signals.

As described in more detail below, although embodiments of the present invention are primarily described in terms of detecting analog clipping and controlling analog clipping of ECG sensor signals, it should be appreciated that the techniques described herein may readily be extended for use with other types of signals, from sensors other than ECG sensing electrodes. For example, aspects of the present invention may be used wherever multiple gain stages are used to amplify signals from other types of sensors, such as activity sensors, multiple axis accelerometers, pulse oxygen sensors, temperature sensors, respiratory rate sensors, thoracic impedance sensors, blood pressure sensors, acoustic sensors, etc.

FIG. 1 illustrates a wearable medical device, such as a LifeVest® Wearable Cardioverter Defibrillator available from ZOLL Medical Corporation of Chelmsford, Mass. in which various aspects of the present invention may be incorporated. As shown, the wearable medical device 100 includes a harness 110 having a pair of shoulder straps and a belt that is worn about the torso of a patient. The harness 110 is typically made from a material, such as cotton, that is breathable, and unlikely to cause skin irritation, even when worn for prolonged periods of time. The wearable medical device 100 includes a plurality of ECG sensing electrodes 112 that are attached to the harness 110 at various positions about the patient's body and electrically coupled to a control unit 120 via a to connection pod 130. The plurality of ECG sensing electrodes 112, which may be dry-sensing capacitance electrodes, are used by the control unit 120 to monitor the cardiac function of the patient and generally include a front/back pair of ECG sensing electrodes and a side/side pair of ECG sensing electrodes. It should be appreciated that additional ECG sensing electrodes may be provided, and the plurality of ECG sensing electrodes 112 may be disposed at varying locations about the patient's body.

The wearable medical device 100 also includes a plurality of therapy electrodes 114 that are electrically coupled to the control unit 120 via the connection pod 130 and which are capable of delivering one or more therapeutic defibrillating shocks to the body of the patient, if it is determined that such treatment is warranted. As shown, the plurality of therapy electrodes 114 includes a first therapy electrode 114a that is disposed on the front of the patient's torso and a second therapy electrode 114b that is disposed on the back of the patient's torso. The second therapy electrode 114b includes a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return.

The connection pod 130 electrically couples the plurality of ECG sensing electrodes 112 and the plurality of therapy electrodes 114 to the control unit 120, and may include electronic circuitry. For example, in one implementation, the connection pod 130 includes signal acquisition circuitry, such as a plurality of differential amplifiers to receive ECG signals from different ones of the plurality of ECG sensing electrodes 112 and to provide a differential ECG signal to the control unit 120 based on the difference therebetween. The connection pod 130 may also include other electronic circuitry, such as a motion sensor or accelerometer by which patient activity may be monitored.

As shown in FIG. 1, the wearable medical device 100 may also include a user interface pod 140 that is electrically coupled to the control unit 120. The user interface pod 140 can be attached to the patient's clothing or to the harness 110, for example, via a clip (not shown) that is attached to a portion of the interface pod 140. Alternatively, the user interface pod 140 may to simply be held in a person's hand. The user interface pod 140 typically includes a number of buttons by which the patient, or a bystander can communicate with the control unit 120, and a speaker by which the control unit 120 may communicate with the patient or the bystander. In certain models of the LifeVest® Wearable Cardioverter Defibrillator, the functionality of the user interface pod 140 is incorporated into the control unit 120.

Where the control unit 120 determines that the patient is experiencing arrhythmia, the control unit 120 may issue an audible alarm via a loudspeaker (not shown) on the control unit 120 and/or the user interface pod 140 alerting the patient and any bystanders to the patient's medical condition. The control unit 120 may also instruct the patient to press and hold one or more buttons on the control unit 120 or on the user interface pod 140 to indicate that the patient is conscious, thereby instructing the control unit 120 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

Figure 2:
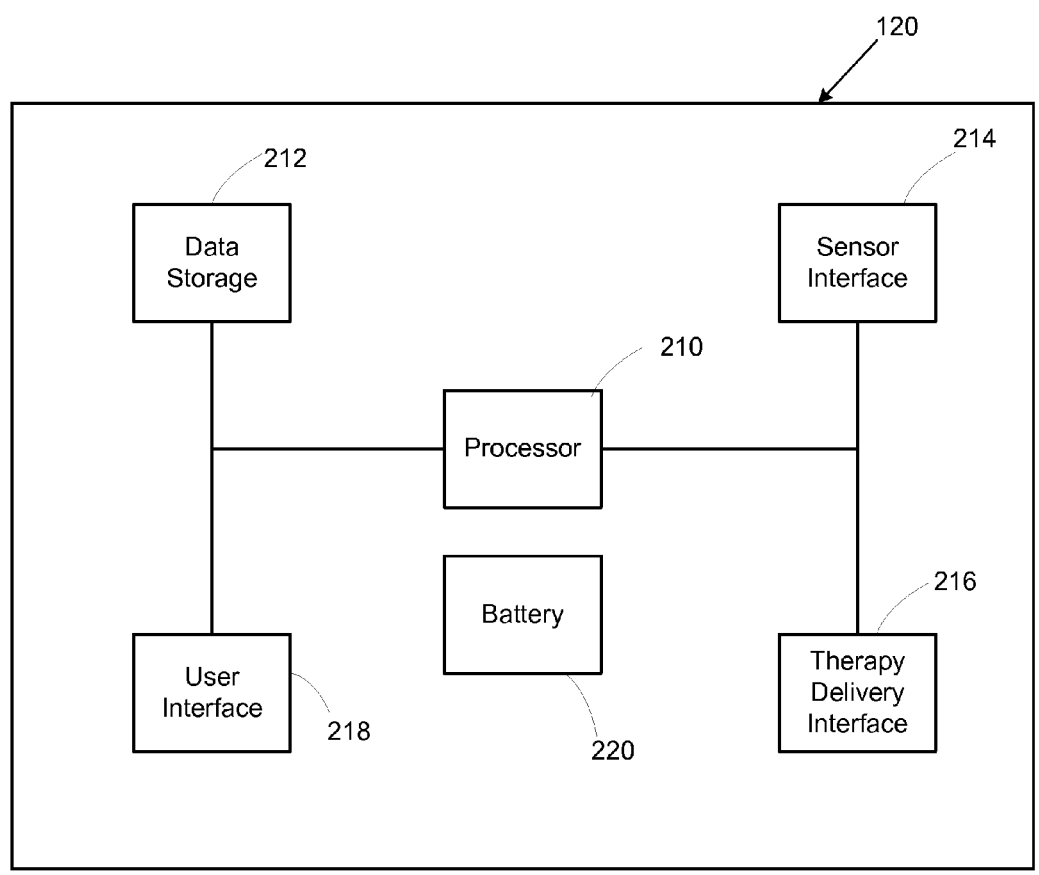
FIG. 2 is a functional block diagram of a control unit that may be used with embodiments of present invention.

FIG. 2 functionally illustrates a control unit, such as the control unit 120 depicted in FIG. 1 that may be used by a portable medical device, such as a wearable defibrillator, in accordance with the present invention. As shown, the control unit 120 includes at least one processor 210, a battery 220, data storage 212, a sensor interface 214, a therapy delivery interface 216, and a user interface 218. The battery 220 may be any type of battery capable of providing electrical power to the other device components, and in one implementation includes a rechargeable three cell 2200 mAh lithium ion battery pack that provides electrical power to the other device components. The data storage 212, the sensor interface 214, the therapy delivery interface 216, and the user interface 218 are coupled to the at least one processor 210. The data storage 212 includes a computer readable and writeable data storage medium configured to store non-transitory instructions and other data, and can include both nonvolatile storage media, such as optical or magnetic disk, ROM or flash memory, as well as volatile memory, such as RAM. The instructions may include executable programs or other code that can be executed by the at least one processor 210 to perform any of the functions described here below.

The at least one processor 210 may be any type of processor, microprocessor, or to controller, such as a microprocessor commercially available from such companies such as Texas Instruments, Intel, AMD, Sun, IBM, Motorola, Freescale, ARM Holdings, etc. In one implementation, the at least one processor 210 includes a power conserving processor arrangement that comprises a general purpose processor, such as an Intel® PXA270 processor and a special purpose processor, such as a Freescale DSP56311 Digital Signal Processor. Such a power conserving processor arrangement is described in co-pending application Ser. No. 12/833,096, titled SYSTEM AND METHOD FOR CONSERVING POWER IN A MEDICAL DEVICE, filed Jul. 9, 2010 (hereinafter the "'096 application") which is incorporated by reference herein in its entirety. The at least one processor of the control unit 120 is configured to monitor the patient's medical condition, to perform medical data logging and storage, and to provide medical treatment to the patient in response to a detected medical condition, such as cardiac arrhythmia.

The therapy delivery interface 216 couples one or more therapy delivery devices, such as defibrillator therapy electrodes 114, to the at least one processor 210. The user interface 218 includes a combination of hardware and software components that allow the control unit 120 to communicate with an external entity, such as a user. These components are configured to receive information from actions such as physical movement or verbal intonation. In addition, the components of the user interface 218 can provide information to external entities, for example, in a manner such as described in U.S. Pat. No. 6,681,003, which is incorporated herein by reference. Examples of the components that may be employed within the user interface 218 include keyboards, mouse devices, trackballs, microphones, electrodes, touch screens, printing devices, display screens and speakers.

The sensor interface 214 couples the at least one processor 210 to a plurality of physiological sensors, such as the plurality of ECG sensing electrodes 112. In some embodiments, the sensor interface 214 may also couple the at least one processor 210 to other physiological sensors, such as activity sensors, pulse oxygen sensors, temperature sensors, respiratory rate sensors, thoracic impedance sensors, blood pressure sensors, acoustic sensors, etc. The sensor interface 214 can include a signal acquisition circuit, such as the signal acquisition circuit shown in FIG. 3 and described further in detail below. The signal acquisition circuit conditions or adjusts the ECG signals before providing the signals to the at least one processor 210.

Figure 3:
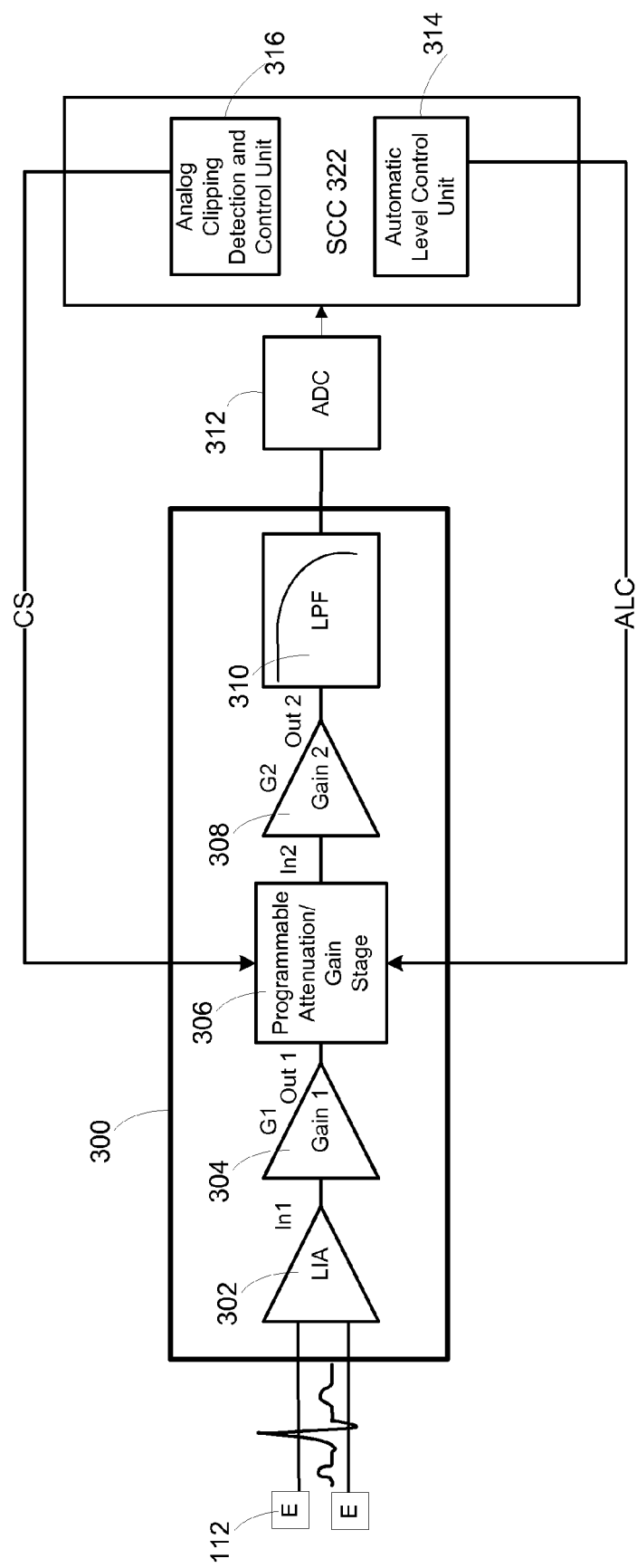
FIG. 3 illustrates a functional block diagram of a signal acquisition circuit to detect and control analog clipping for use with a wearable medical device in accordance with an embodiment of the present invention.

FIG. 3 illustrates a signal acquisition circuit 300 that may be used with a plurality of ECG sensors in accordance with an aspect of the present invention to condition or adjust the ECG signal. Although only a single signal acquisition circuit 300 is depicted in FIG. 3, it should be appreciated that in a typical implementation, multiple signal acquisition circuits 300 would be provided for each pair of ECG sensing electrodes 112. As shown, the signal acquisition circuit 300 includes a low noise instrumentation amplifier (LIA) 302, a first gain stage 304, a programmable attenuation/gain stage 306, a second gain stage 308, and a low pass filter (LPF) 310. The signal acquisition circuit 300 is electrically coupled to an analog to digital converter 312 (ADC) that provides a digitized ECG signal to the at least one processor 210 (FIG. 2). The digitized ECG signal is also provided to a signal conditioning and control unit (SCC) 322 that is responsible for monitoring and controlling the ECG signal at various stages of the signal acquisition circuit. The SCC 322 includes an automatic level control unit (ALC) 314 and an analog clipping detection and control unit (ACDC) 316. In accordance with one embodiment, the SCC unit 322 is capable of controlling the ECG signal at each stage of the signal acquisition circuit, as described further below. The SCC unit 322 may be implemented as a series of instructions that are performed by the at least one processor 210 or as a dedicated logic circuit.

In one embodiment, the signals from each of the plurality of ECG sensing electrodes 112 are provided to a respective input of the LIA 302 of the signal acquisition circuit 300. Although not depicted in FIG. 3, each of the plurality of ECG sensing electrodes 112 may be electrically coupled to a respective buffer amplifier, with the output of each respective buffer amplifier being electrically coupled to a respective input of the LIA 302. The inclusion of such a buffer amplifier, which may have unity gain, provides a very high impedance input to each respective output of an ECG sensing electrode. The LIA 302 is a differential amplifier that obtains the difference between the signals received on each respective input of the LIA 302, which typically, are 180 degrees out of phase with one another. The LIA 302 automatically cancels out the common mode noise from the incoming ECG signal. The LIA 302 may be selected for additional desirable characteristics such as low DC offset, low drift, low noise, and to high common-mode rejection ratio. In some embodiments, the LIA 302 may also provide some amount of gain, which in one embodiment, may be approximately five times the input.

In one embodiment, the LIA 302 is electrically coupled to the first gain stage 304 that further amplifies the ECG signal. The first gain stage 304 may be a single amplifier or a series of amplifiers. The first gain stage 304 multiplies the input voltage level obtained from the LIA 302 by a predetermined amount of gain, G1. In one embodiment, the first gain stage provides a gain of approximately 28 times the input.

The first gain stage 304 is electrically coupled to the programmable attenuation/gain stage 306 that applies a varying amount of attenuation to the ECG signal based on a control signal from the ALC 314. The programmable attenuation/gain stage 306 may alternatively provide some amount of gain.

Although not depicted in FIG. 3, in accordance with one embodiment, a programmable filter may be electrically coupled between the first gain stage 304 and the programmable attenuation/gain stage 306. The programmable filter may be a programmable low pass filter with a programmable cut-off frequency, or a programmable notch filter with a programmable center frequency. For example, where there is an indication of high frequency noise at the output of the first gain stage 304, the cutoff frequency of the programmable filter may be lowered (or the center frequency adjusted) to filter out the noise. The programmable filter may also be comprised of multiple filters such as a band pass filter with an integrated band stop filter to reject a specific frequency or frequencies such as 60 and 120 Hz while allowing other frequencies in a range from about 0.5 Hz to 100 Hz or from about 0.5 Hz to 200 Hz.

The ECG signal may experience rapid and wide variations in amplitude due to interference from unrelated signals. For example, the ECG signal may include noise due to a nearby electronic device. ECG signal noise can also be caused by electrodes sliding on the patient's body due to extreme patient movement, such as vigorous exercise. A poorly fit electrode belt or garment can allow the electrodes to slide on the patient's body even with minor patient movement. Typically, the dynamic range of the signal acquisition circuit 300 is limited and not suited to accommodate large fluctuations of the signal input. The ALC 314 allows the signal acquisition circuit 300 to use the entire dynamic range of the ECG signal by controlling the amount of attenuation provided at the programmable attenuation/gain stage 306. The signal acquisition circuit 300 is configured to detect ECG signals between the range of about 100 microvolts and about 5 millivolts, with signals below about 80 microvolts being considered to be indicative of an asystolic condition. To perform automatic level control of the ECG signal, the ALC 314 varies the amount of attenuation applied at the programmable attenuation/gain stage 306 depending on the level of the output signal provided by the ADC 312. If the ALC 314 determines that the voltage level of the ECG signal provided by the ADC is too high, the ALC 314 can send a control signal to the programmable attenuation/gain stage 306 to increase the amount of attenuation applied to the ECG signal. In contrast, if the voltage level of the ECG signal is too low, the ALC 314 can send a control signal to the programmable attenuation/gain stage 306 to decrease the amount of attenuation to the ECG signal.

The programmable attenuation/gain stage 306 is electrically coupled to the second gain stage 308 that further amplifies the ECG signal. Similar to the first gain stage 304, the second gain stage 308 may include a single amplifier or a series of amplifiers. The second gain stage 308 multiplies the input voltage level received from the programmable attenuation/gain stage 306 by a predetermined amount of gain, G2. In one embodiment, the second gain stage 308 provides a gain of approximately 12 times the input. It is appreciated, that in some embodiments the programmable attenuation/gain stage 306 may be included as one of the amplifiers in the first gain stage 304, or the second gain stage 308. In some embodiments, the first gain stage 304 and the second gain stage 308 may include a programmable gain stage.

The second gain stage 308 is electrically coupled to the LPF 310. The LPF 310 is designed to reduce or eliminate high frequency noise and to protect the ADC 312 from ECG signals that would cause aliasing. For example, ECG signals having a frequency of more than half of the sample rate of the ADC can cause aliasing. In one exemplary embodiment, the LPF 310 has a bandwidth of approximately 100 Hz and a cutoff frequency at approximately 100 Hz. In some implementations, the LPF may be implemented as part of the second gain stage 308. In accordance with one embodiment, the LPF may be a programmable LPF having a programmable cutoff frequency that can be controlled by the SCC 322. The LPF 310 is electrically coupled to an input of the ADC 312. The ADC 312 digitizes the analog ECG signal to a digital signal and may further condition the signal prior for further analysis and monitoring by the at least one processor 210, as described above.

The functionality of the ACDC 316 to detect and correct analog clipping is described below. For clarity, the voltage level at the input of second gain stage 308 is labeled as IN2, the gain of the second gain stage 308 as G2 and the voltage level at the output of the second gain stage 308 as OUT2. The voltage level at the input of first gain stage 304 is labeled as IN1, the gain of the first gain stage 304 as G1 and the voltage level at the output of the first gain stage 304 as OUT1.

The ACDC 316 unit first calculates ECG voltage levels IN1, IN2, OUT1 and OUT2 at each of the gain stages based upon the voltage levels of the ECG signal at the output of the ADC 312 and the predetermined gain values, G1 and G2, as well as, the attenuation setting set by the ALC 314. The ACDC 316 then determines whether the voltage levels at each of the gain stages are approaching or are at the analog clipping thresholds at the first and second gain stages.

If the voltage level is approaching the clipping threshold after the programmable attenuation/gain stage 306, the ACDC 316 can send a control signal (CS) to the programmable attenuation/gain stage 306 to provide additional attenuation to the ECG signal provided at OUT1. Additional attenuation will prevent analog clipping of the signal at the second gain stage 308, IN2. In addition, where a programmable LPF 310 is used and the SCC 322 detects the presence of high frequency noise, additional analysis of the LPF input and output may be performed to determine if the high frequency noise is causing clipping. Should it be determined that high frequency noise is causing clipping, the SCC 322 may lower the cutoff frequency of the LPF 310.

By contrast, if the voltage levels are approaching or are at the clipping threshold before the programmable attenuation/gain stage 306, the sampled data at the ADC 312 is marked as compromised or corrupted to prevent mis-detection by the at least one processor 210. The ACDC 316 will continue to monitor the analog signal at the first gain stage 304 until the ECG signal returns to a level sufficiently below the analog clipping threshold. The ALC 314 functionality may be turned off until the ECG voltage level returns to below the threshold levels. Once the ECG signal at the first gain stage 304 is sufficiently below the threshold, the ALC 314 may be turned on and normal operation of the system may resume.

In some embodiments, where the first gain stage 304 and the second gain stage 308 are to both programmable gain/attenuation stages, the programmable attenuation/gain stage 306 may not be needed. In this embodiment, the ACDC 316 can determine whether voltage levels are approaching or are at the analog clipping thresholds at either the first or second programmable attenuation/gain stages. Where it is determined that the voltage level is approaching the clipping threshold at the first attenuation/gain stage, the ACDC 316 can send a control signal to the first attenuation/gain stage to reduce the amount of gain at the first attenuation/gain stage. Where it is determined that the voltage level is approaching the clipping threshold at the second attenuation/gain stage, the ACDC 316 can send a control signal to the second attenuation/gain stage to reduce the amount of gain at the second attenuation/gain stage. The reduction in gain can prevent analog clipping of the signal at either the first or the second attenuation/gain stages.

Values for the clipping threshold for the first gain stage 304 may be predetermined based on the voltage range of a typical human ECG and the maximum output level of the gain stage amplifiers that are used in the signal acquisition circuit 300. For example, human ECG voltage levels are typically between about 80 microvolts and about 2 millivolts in amplitude. Due to the high gain required for processing the ECG signal, the gain stage amplifiers may start clipping when the analog signals received by the LIA 302 have amplitude of about 70 millivolts or more. Because ECG signals above approximately 2 millivolts are well outside the normal range of a human ECG signal, any input voltages provided to the LIA 302 that exceed this value may be considered corrupted. Such corrupted data can be flagged or marked to indicate to the at least one processor 210 that the data should not be used to determine proper treatment procedure. During this period of time, the functionality of the ALC 314 may be disabled until normal levels at the output of the LIA 302 return.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A wearable medical device, comprising:
    a plurality of ECG sensing electrodes configured to sense an ECG signal of a patient;
    an ECG acquisition circuit, electrically coupled to a pair of the plurality of ECG sensing electrodes, including a first gain stage to amplify the ECG signal, a programmable attenuation/gain stage coupled to the first gain stage to condition the amplified ECG signal, and a second gain stage coupled to the programmable attenuation/gain stage to amplify the conditioned ECG signal;
    an analog to digital converter, electrically coupled to the ECG acquisition circuit, to receive and digitize the amplified and conditioned analog ECG signal and provide a digitized ECG signal; and
    a signal conditioning and control unit, electrically coupled to the ECG acquisition circuit and the analog to digital converter, to monitor the digitized ECG signal, to determine whether a voltage level of the ECG signal is approaching a first threshold based on at least the digitized ECG signal, and to mark the digitized ECG signal as compromised in response to a determination that the voltage level of the ECG signal is approaching the first threshold to alert the wearable medical device that the digitized ECG signal is distorted.

2. The wearable medical device of claim 1, wherein the signal conditioning and control unit is configured to vary an amount of attenuation/gain provided by the programmable attenuation/gain stage based on the digitized ECG signal.

3. The wearable medical device of claim 2, wherein the signal conditioning and control unit is configured to determine whether a voltage level of the digitized ECG signal is above a second threshold, and to increase the amount of attenuation provided by the programmable attenuation/gain stage.

4. The wearable medical device of claim 2, wherein the signal conditioning and control unit is configured to determine whether a voltage level of the digitized ECG signal is below a second threshold, and to decrease the amount of attenuation provided by the programmable attenuation/gain stage.

5. The wearable medical device of claim 1, wherein the signal conditioning and control unit is configured to determine the first threshold based on at least one of a voltage range of an ECG of a human patient, a current gain setting and a maximum output voltage level of at least one of the first gain stage, the programmable attenuation/gain stage and the second gain stage.

6. The wearable medical device of claim 1, wherein the signal conditioning and control unit is configured to determine whether a voltage level of the conditioned ECG signal is approaching a second threshold based on at least the digitized ECG signal.

7. The wearable medical device of claim 6, wherein the signal conditioning and control unit is configured to attenuate the amplified and conditioned analog ECG signal in response to a determination that the voltage level is approaching the second threshold.

8. The wearable medical device of claim 6, wherein the signal conditioning and control unit is configured to determine the second threshold based on at least one of a voltage range of an ECG of a human patient, a current gain setting and a maximum output voltage level of at least one of the first gain stage, the programmable attenuation/gain stage and the second gain stage.

9. The wearable medical device of claim 1, wherein the signal conditioning and control unit is configured to detect high frequency noise in the ECG signal and adjusting a cutoff frequency of a filter responsive to detecting the high frequency noise.

10. The wearable medical device of claim 1, wherein the signal conditioning and control unit is configured to determine whether clipping of the amplified and conditioned ECG signal occurred before or after the programmable attenuation/gain stage.

11. The wearable medical device of claim 10, wherein the signal conditioning and control unit is configured to mark the amplified and conditioned ECG signal as compromised in response to a determination that the clipping of the amplified and conditioned ECG signal occurred before the programmable attenuation/gain stage.

12. The wearable medical device of claim 10, wherein the signal conditioning and control unit is configured to attenuate the amplified and conditioned ECG signal in response to a determination that the clipping of the amplified and conditioned ECG signal occurred after the programmable attenuation/gain stage.

13. The wearable medical device of claim 10, wherein the signal conditioning and control unit is configured to attenuate the amplified and conditioned ECG signal in response to a determination that the clipping of the amplified and conditioned ECG signal occurred after the programmable attenuation/gain stage and wherein the signal conditioning and control unit is configured to mark the amplified and conditioned ECG signal as compromised in response to a determination that the clipping of the amplified and conditioned ECG signal occurred before the programmable attenuation/gain stage.

* * * * *